United States Patent [19]

Frankel et al.

[11] 4,268,450

[45] May 19, 1981

[54] ENERGETIC HYDROXY-TERMINATED AZIDO POLYMER

[75] Inventors: Milton B. Frankel, Tarzana; Joseph E. Flanagan, Woodland Hills, both of Calif.

[73] Assignee: Rockwell International Corporation, El Segundo, Calif.

[21] Appl. No.: 4,978

[22] Filed: Jan. 8, 1979

Related U.S. Application Data

[63] Continuation-in-part of Ser. No. 822,490, Aug. 8, 1977, abandoned.

[51] Int. Cl.³ .................... C07C 117/00; C08G 65/32; C08G 65/22; C08G 65/24
[52] U.S. Cl. .................... 260/349; 149/196; 525/403; 525/410; 526/273; 528/417; 528/421
[58] Field of Search ............... 525/410, 403; 260/349; 149/19.6; 526/273; 528/417, 421

[56] References Cited

U.S. PATENT DOCUMENTS

| | | | |
|---|---|---|---|
| 2,948,610 | 8/1960 | Merrill et al. | 260/349 |
| 3,122,570 | 2/1964 | Stansbury et al. | 260/349 |
| 3,453,108 | 7/1969 | Delzenne et al. | 260/349 |
| 3,645,917 | 2/1972 | Vandenberg | 525/410 |
| 3,849,230 | 11/1974 | Breslow | 260/349 |
| 4,031,068 | 6/1977 | Cantor | 260/349 |
| 4,085,123 | 4/1978 | Flanagan et al. | 260/349 |
| 4,141,910 | 2/1979 | Flanagan et al. | 260/349 |

*Primary Examiner*—Teddy S. Gron
*Attorney, Agent, or Firm*—H. F. Hamann; Harry B. Field

[57] ABSTRACT

An energetic binder comprises a hydroxy-terminated aliphatic polymer having pendant alkyl azide groups and method for producing same.

4 Claims, No Drawings

ENERGETIC HYDROXY-TERMINATED AZIDO POLYMER

CROSS REFERENCE TO RELATED APPLICATIONS

This application is a continuation-in-part of Ser. No. 822,490 filed Aug. 8, 1977 abandoned July 3, 1980.

BACKGROUND OF THE INVENTION

1. Field of the Invention

This invention relates to composition of matter, and is particularly directed to the disclosure of an energetic binder comprising hydroxy-terminated aliphatic polyethers having pendant alkyl azide groups, together with a method for producing this compound.

2. Description of the Prior Art

Solid propellants are formulated from an oxidizer and fuel together with suitable binders and plasticizers to impart physical integrity. Most highly energetic systems utilize binders and plasticizers containing energetic groups such as nitro (—$NO_2$), fluorodinitro ($FC(NO_2)_2$—), difluoroamino (—$NF_2$), and many others.

Utilization of azido plasticizers has become a reality during the last several years. These azido plasticizers impart additional energy to propellants since each azido group present adds approximately 85 kcal/mole of energy to the system. It follows that utilization of an azido polymer would impart additional energy to the system. Unfortunately, the few azido polymers synthesized to date are not functionally terminated which is a necessity for good propellant castability and physical properties.

One functionally terminated azido polymer is taught by Delzenne et al, U.S. Pat. No. 3,453,108. In contrast to the presently claimed hydroxy-terminated aliphatic polyether having directly pendant alkyl azide groups, Delzenne et al teach azidosulphonyl substituents connected through an aromatic ring structured to the polymer backbone. In that this polymer has a completely different structural formula, completely different chemical and physical properties, as well as a completely different use, its teaching would not render obvious the presently claimed invention.

SUMMARY OF THE INVENTION

Accordingly there is provided by the present invention an energetic polymer comprising a hydroxy-terminated aliphatic polymer having pendant alkyl azide groups, such as $(CH_2)_nN_3$, and $CH_2CHN_3CH_2N_3$ wherein n is an integer from 1 to 5, and a method for preparing same.

OBJECTS OF THE INVENTION

Therefore, it is an object of the present invention to provide improved materials for formulating solid propellants.

Another object of the present invention is to provide a new composition of matter.

An additional object of the present invention is to provide an energetic azido polymer.

A specific object of the present invention is to provide a hydroxy-terminated aliphatic polyether having pendant alkyl azide groups.

These and other objects and features of the present invention will be apparent from the following detailed description.

DESCRIPTION OF THE PREFERRED EMBODIMENTS

In accordance with the present invention there is provided a hydroxy-terminated or carboxy-terminated aliphatic polymer having pendant alkyl azide groups. Although almost any polymer will work, polyethers and polyesters are preferred, and polyether is most preferred. Basically the hydroxy-terminated aliphatic polyethers having pendant alkyl azide groups has the following structural formula:

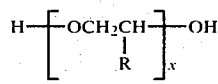

wherein R is represented by alkyl azides such as —$(CH_2)_nN_3$, and —$CH_2CHN_3CH_2N_3$, wherein n is an integer from 1 to 5, and wherein x is an integer from 10 to 60. In its preferred configuration, the hydroxy-terminated aliphatic polyether of the present invention will have the following structural formula:

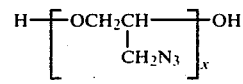

wherein x is an integer from 20 to 40.

In general, the desired hydroxyl-terminated aliphatic polyether having pendant alkyl azide groups is prepared as follows:

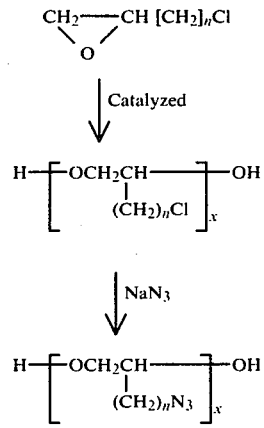

wherein n is an integer from 1–5 and x is an integer from 10 to 60. A typical catalyst for this system would be $BF_3$. Similarly, the alkyl diazido polymer can be prepared by starting with a dichloro compound such as

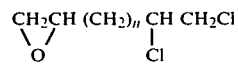

One such commercially available compound is 1,2-diepoxy-4,5-dichloropentane.

By way of example and not limitation, the azido polymer of the present invention can be prepared as follows:

A mixture of 100 g (1.0 mole) of polyepichlorohydrin, 130 g (2.0 moles) of sodium azide, and 600 ml of dimethyl formamide was heated at 100° C. and agitated for 72 hours. The mixture was cooled and diluted with 500 ml of methylene chloride. The reaction mixture was then washed with water to remove sodium azide and dimethylformamide. The methylene chloride solution was dried over magnesium sulfate and concentrated to give 78 g (72.9%) of viscous amber liquid.

The liquid was characterized and the following properties were obtained:

Elemental Analysis: C(36.21); H(5.05); N(40.56) wt.%
Molecular Weight: 2500
Functionality: 2
Infrared Spectrum: 4.75 μ(s) for $N_3$
Density: 1.30 gm/cc Obviously, numerous variations and modifications may be made without departing from the present invention. Accordingly, it should be clearly understood that the form of the present invention described above is illustrative only and is not intended to limit the scope of the present invention.

We claim:

1. A hydroxy-terminated aliphatic polyether having pendant alkyl azide groups has a general structural formula of:

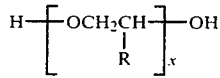

wherein x is an integer from 10 to 60 and wherein R is selected from the group consisting of —$(CH_2)_nN_3$, and —$CH_2CHN_3CH_2N_3$, and wherein n is an integer from 1 to 5.

2. The hydroxy-terminated aliphatic polyether of claim 1 having a structural formula of:

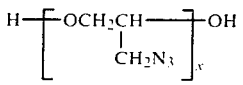

wherein x is an integer from 10 to 60.

3. The hydroxy-terminated aliphatic polyether of claims 1 or 2 wherein x is an integer from 20 to 40.

4. A process for producing hydroxy-terminated aliphatic polyethers of the general formula

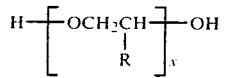

by reacting a compound of the general formula

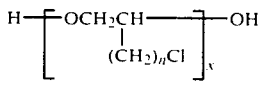

with sodium azide in an appropriate polar organic solvent wherein x is an integer from 10 to 60 and wherein R is selected from the group consisting of —$(CH_2)_nN_3$ and —$CH_2CHN_3CH_2N_3$, and wherein n is an integer from 1 to 5.

* * * * *